United States Patent [19]

Linggood et al.

[11] Patent Number: 4,971,794

[45] Date of Patent: Nov. 20, 1990

[54] **PRODUCTION OF ANTIBODIES USING A MIXTURE OF STRAINS OF *E. COLI* COLLECTIVELY EXPRESSING TYPE I PILI, CFA I PILI, CFA II PILI AND K88 PILI**

[75] Inventors: Margaret A. Linggood, Bedfordshire; Philip Porter, Bedford; Jonathan R. Powell, Bedfordshire, all of United Kingdom

[73] Assignee: Unilever Patent Holdings B.V., Rotterdam, Netherlands

[21] Appl. No.: 933,358

[22] Filed: Nov. 19, 1986

Related U.S. Application Data

[63] Continuation of Ser. No. 738,516, May 28, 1985, abandoned, which is a continuation of Ser. No. 525,824, Aug. 23, 1983.

[51] Int. Cl.$^5$ .................... A61K 35/74; A61K 39/108
[52] U.S. Cl. ...................................... 424/92; 424/85.8; 424/88; 424/93; 435/252.33; 435/848; 435/849
[58] Field of Search ..................................... 424/85-92

[56] References Cited

U.S. PATENT DOCUMENTS 3,128,230  4/1964  Heinboch ............................ 424/89
4,237,115 12/1980  Brinton, Jr. ......................... 435/820
4,298,597 11/1981  Acres et al. ......................... 424/92
4,343,792  8/1982  Gouet et al. ........................ 424/92
4,411,888 10/1983  Klipstein et al. .................... 424/92

FOREIGN PATENT DOCUMENTS 0048881  4/1982  European Pat. Off. .
1472624  5/1977  United Kingdom .

OTHER PUBLICATIONS

Gaastra et al., Microbiological Reviews, Jun. 1982, pp. 129-161.

*Primary Examiner*—Margaret Moskowitz
*Assistant Examiner*—Jeff Kushan
*Attorney, Agent, or Firm*—Cushman, Darby & Cushman

[57] ABSTRACT

Antibodies are produced by hyperimmunizing a mammal, such as cow, with a vaccine derived from *E. coli* bacteria. The bacterial strains in the vaccine are selected on the basis of their virulence characteristics, especially adhesion factors (pili), associated with gastroenteric disease in humans. The antibodies can be recovered from the mammal's milk or serum, and used in human foods.

13 Claims, No Drawings

PRODUCTION OF ANTIBODIES USING A MIXTURE OF STRAINS OF E. COLI COLLECTIVELY EXPRESSING TYPE I PILI, CFA I PILI, CFA II PILI AND K88 PILI

This is a continuation of application Ser. No. 738,516, filed May 28, 1985, which was abandoned upon the filing thereof, and which is itself a continuation of Ser. No. 525,824 filed Aug. 23, 1983.

The present invention relates to the production of antibodies.

The mammalian defense mechanism against many diseases, including those caused by bacteria such as *Escherichia coli*, involves the production of antibodies known as immunoglobulins. Several distinct classes of immunoglobulins, of which the commonest are referred to as IgA, IgG, IgM, IgD, and IgE, have been identified. Not all mammalian species produce the same range of immunoglobulins, and some species apparently place greater reliance on one particular immunoglobulin rather than on another, type that may predominate in the defence mechanisms of other mammalian species.

The immunoglobulins, which are complex protein structures, circulate in the mammal's bloodstream, and in the lactating female are important constituents of her milk, especially in the colostrum (first milk) produced during the first few days following the birth of an infant. The suckling infant ingests these immunoglobulins, and thereby derives passive immunity against, in particular, enteropathogenic bacteria. This is highly important, because it may be several days or even weeks before the infant's own immune mechanisms are sufficiently stimulated for it to generate its own antibodies in effective quantities. In this way, the breast-fed human infant derives passive immunity against gastro-entestinal infections because its mother's milk contains substantial quantities of appropriate immunoglobulins.

As an alternative to breast-feeding, it is common practice to use bovine milk as a substitute for human milk, either consumed as such or in the form of synthetic milks based on bovine milk, i.e. skimmed milk powder. In many parts of the world, the milk from other mammals, such as goats, is used.

Natural bovine milk also contains immunoglobulins designed by nature to protect the calf in a similar manner. However, the relative concentrations of immunoglobulins in bovine milk differ from those in human milk. The immunoglobulin (IgA) predominates in human milk and lines the intestinal mucosa of the infant and provides very efficient long-term protection, but bovine milk contains lower levels of IgA. Bovine milk, and in fact the milk of ruminant animals generally, is rich in the immunoglobulin $IgG_1$ which is closely related to but not identical with the immunoglobulin IgG that occurs in minor proportions in human milk. $IgG_1$ only remains in the lumen of the intestine, and provides comparatively short-term protection against gastrointestinal infections in the human. Furthermore, the specific immunoglobulins present in bovine milk are raised by the cow against its own pathogens, and not against those that commonly infect the human.

A further problem is that the normal processing to which bovine milk is subjected in Western countries, e.g. pasteurisation or sterilisation in the case of whole milk and also spray-drying in the case of milk powder, usually involves temperature conditions that are sufficiently extreme to destroy the beneficial activity of any immunoglobulins present in the original milk. Therefore the natural protection afforded by these immunoglobulins is usually lost.

It has been proposed to supplement the immunoprophylactic activity of milk and milk substitutes for human use by the addition thereto of concentrates derived from bovine milk, containing the natural bovine immunoglobulins in active form. This will indeed provide some measure of passive immunity, but the concentrate will contain in addition to the desirable immunoglobulins many other trace ingredients of natural milk. Moreover, as has already been indicated, the immunoglobulins present in bovine milk are not those of prime importance to the human infant.

To improve this situation it has been proposed to hyperimmunise milk-producing animals, especially cattle, by means of vaccines prepared from known human gut pathogens, with the objective of causing the animal to produce antibodies that are more specific to and hence more effective against the human pathogens. This approach is described in UK patent specification No. 1 573 995 (Societe des Produits Nestle SA; inventor different strains of *E. coli*, selected probably because they had been most commonly identified in the literature as being implicated in outbreaks of human gastroenteric disease.

Gastro-enteric disorders in human adults and in human infants have been the subject of extensive research, but a study of the scientific literature reveals a wide divergence of views amongst the experts in this field as to which strains of micro-organisms are principally implicated in causing such disorders. In view of the large number of bacterial strains that are apparently implicated, and in view of the confusion that is generated by reading the diverse opinions on this topic as expressed in the scientific literature, it is no simple matter to identify a narrow selection of key bacterial strains that is likely to provide the basis of a vaccine that will impart immunity against a broad spectrum of gut microorganisms. From the economic standpoinct, the number of stains involved in the selection should be kept to a minimum. From the standpoint of efficacy, the vaccine should impart immunity against as many gut-infective strains of micro-organisms as possible. No such simple selection can be derived from the present knowledge as recorded in the scientific literature. On the contrary, it would seem from the published data that a very large number of different strains would have to be involved in order to provide broad immunity in the human. This is in line with the approach adopted by Hilpert.

We now provide the means for selecting appropriate stains, based on their virulence characteristics.

The invention provides a process for the preparation of immunoglobulins useful in providing passive protection against *E. coli* bacteria implicated in causing gastroenteric disease in humans, in which process a host mammal is immunised with a vaccine comprising antigens of at least two strains of *E. coli* expressing collectively chromosome-mediated adhesion factors (pili) and plasmid-mediated adhesion factors (pili) to induce the host mammal to produce substantial quantities of immunoglobulins specific to the antigens, and the immunoglobulins are recovered in functional form.

Preferably the chromosome-mediated adhesion factors expressed by at least one of the bacterial strains from which the vaccine is derived, include Type I pili.

Preferably the plasmid-mediated adhesion factors expressed by the bacterial strains from which the vaccine is derived, include CFA I pili and/or CFA II pili.

In a particularly preferred embodiment of the invention, the vaccine comprises antigens of a plurality of bacterial strains expressing collectively Type I pili, CFA I pili, CFA II pili and K88 pili.

Preferably the vaccine used includes antigens of at least one bacterial strain that produces enterotoxins, ideally of both the heat-stable (ST) and heat-labile (LT) types. This requirement is secondary to the pili-expression criteria set out above. Preferably, at least one of the selected bacterial strains is also a producer of enterotoxins.

An important product of the invention is non-human milk incorporating immunoglobulins active against a plurality of *E. coli* strains implicated in causing gastroenteric disease in humans, expressing collectively the pili of the types Type I CFA I and CFA II.

A further product of the invention is immunoglobulin material that has been prepared as described in the immediately proceeding paragraphs. Such immunoglobulin material can be added to human foodstuffs to provide passive immunity against gut infective bacteria. The immunoglobulin material can be recovered from immune milk by conventional methods involving concentration, precipitation or chromatographic techniques. Alternatively, although less desirably, the immunoglobulin material can be recovered from serum derived from the host animal, in which case a non milk producing (or indeed male) host animal can be used.

A further embodiment of the invention is a food product for humans, and especially a milk substitute formulated for human infants, containing recovered immunoglobulin material as just described. Such milk substitutes can be manufactured and marketed in liquid form, but more commonly are provided in the form of dry powders requiring reconstitution in water.

An important aspect of the invention is a vaccine for oral and/or parenteral administration comprising, in a pharmaceutically acceptable carrier or diluent, antigens of a plurality of *E. coli* strains collectively expressing at least one virulence characteristic selected from each of the following groups:
(a) chromosome-mediated pili,
(b) CFA I pili and CFA II pili,
(c) K88 pili and plasmid-mediated pili of the antigenic type expressed by 0159 *E. coli* strain E2985/76.

A further important embodiment of the invention is a process for the preparation of an oral product for humans, capable of imparting passive protection against *E. coli* bacteria implicated in causing gastroenteric disease in humans, in which process a milk-producing host mammal selected from the group consisting of the Bovidae is immunised with a vaccine comprising antigens of at least one *E. coli* strain selected from each of the following groups:
(a) a Type 1 pili expressing *E. coli* of the serogroups 018 and 0125,
(b) a CFA I pili expressing *E. coli* of the serogroups 025 and 078, and
(c) a CFA II pili expressing *E. coli* of the serogroups 06 and 08,
to induce the host mammal to produce substantial quantities of immunoglobulins specific to the antigens, milk from the host mammal is collected, and the immunoglobulins are recovered in functional form from the milk and formulated into an orally ingestable product in an amount sufficient to provide passive protection.

Pili are proteinaceous features on the exterior of bacterial cells that are in some way associated with the ability of the living bacteria to cling to the gut wall. Under the electron microscope, pili appear as spine-like projections on the surface of the bacterium. The expression of pili types CFA (Colonisation Factor Antigen) I and CFA II and K88 appear to be dictated by plasmid-born genetic information, and for this reason this characteristic appears to be transmissable from one strain to another. However, as far as we are aware a given *E. coli* strain will express CFA I pili, or CFA II pili or K88 pili but not two or more types simultaneously. Many *E. coli* strains do not express any of these types. In view of the transmissible nature of this characteristic, and hence the fact that a given strain of *E. coli* that may previously have been identified as expressing for example CFA I pili may later lose the relevant plasmid-born genetic information and therefore cease to express such pili, it is important to check positively by regular tests, e.g. using antisera as described below, that the relevant strains involved in vaccine production are indeed still exhibiting their essential characteristics.

The expression of Type I pili appears to be dictated by chromosomal genetic information, and this characteristic is not transmissable from one strain to another. Some *E. coli* strains express Type I pili only and some *E. coli* strains that normally express CFA I, CFA II or K88 pili also express (or at least have the potential to express) Type I pili. In the art, Type I pili are sometimes referred to as "Common pili"; when first identified, they were found to be common to more than one *E. coli* serotype.

These four classes of pili (Type I, CFA I/II and K88) are familiar bacterial characteristics and are fully described in the scientific literature. For example, Type I pili are described by Brinton, C.C. in *Nature*, 1959, Vol. 183, pages 782–786 and further by Brinton in *Proc. 13th Joint US/Japan Conference on Cholera*, (1978) NIH Bethesda 78-1590 pages 33–70. CFA I pili are described by Evans, D. G. et al. in *Infection and Immunology*, 1975, Vol. 12, pages 656–667. CFA II pili are described by Evans D. G. and Evans D. J. in *Infection and Immunology*, 1978, Vol. 21, pages 638–647. K88 pili are described in Orskov, I. and Orskov, F. in *J. Bacteriol*, 1966, Vol. 91, pages 66–75 and by Stirm et al. in *J. Bacteriol*, 1967, Vol. 93, pages 740–748.

The term "antigen" is used herein to mean any antigenic material naturally generated by bacteria in the live state. Such material can be present on the exterior of the bacterium, excreted by the living organism, or can normally be present only within the body of the organism. It will be appreciated that the vaccine should not comprise viable pathogenic organisms, and hence the usual way in which an appropriate vaccine will be produced will include the step of killing, or at least attenuating, the pathogens so as to render them effectively harmless. This step will also often lead to substantial release of antigenic material from physical association with the bacterial cells. For example, killing the bacteria by means of heat causes the release of large quantities of pili and endotoxins from the bacterial cell. Such released antigenic material can be used as the sole active constituent of the vaccine if desired, but the separation of the killed or attenuated bacterial cells is not strictly necessary and indeed the cell debris will generally contribute usefully to the antigenic character of the vaccine. Whatever the composition of the vaccine, it is most preferable that it should include pili material.

There are various options open for exposing the host animal to the antigens in order to promote the production of appropriate antibodies. One method is to infect the gastro-intestinal system of the host animal with one or more strains of *E. coli* that are implicated in causing gastro-intestinal infections in the human. However, in view of the species specificity of most bacterial strains, and for general health reasons, such a procedure is not particularly desirable.

Alternatively, killed or inactivated bacteria, and/or antigens released from the bacteria, can be administered, in an appropriate carrier or diluent, orally to the host animal in order to promote an appropriate response by the host's immune system. For example, endotoxins can be released from the relevant bacteria when they are killed by means of heat, and the endotoxins can for example be incorporated in a feedstuff for the host animal. The killed bacteria can also be incorporated in the diet to enhance the immune response further. Alternatively, the vaccine can be presented in the form of an oral medicament such as a pill, capsule, powder or liquid. An aqueous solution or suspension of antigenic material can be used. Relatively large doses of vaccine can be administered orally without risk.

A third alternative is to administer parenterally an injectable composition containing killed or inactivated bacteria and/or antigens released therefrom, in a pharmaceutically acceptable carrier or diluent, such as water. The presence of this composition in the body of the host will also promote an appropriate immune response and result in the production of the required antibodies. Injection tends to produce a more immediate and efficient response, although the magnitude of the dose may need to be limited due to sensitivity of the host animal. The injection can be effected by any convenient route, such as intravenous, intramuscular, subcutaneous or intramammary. The vaccine composition can include a wide variety of standard injectable vaccine adjuvants, such as gums and proteins, inorganic adsorbents such as aluminium hydroxide, and oil-water emulsions such as Freund's adjuvant (preferably in its incomplete form). These adjuvants can enhance the efficacy of the vaccine response or provide a delayed release to prolong the effect of the injection. The vaccine can also incorporate preservatives, such as phenol or formalin.

When an injectable or oral vaccine is used to immunise a milk-producing mammal from whose milk it is intended to recover the required immunoglobulins, it is preferable that the immunisation should be performed, or at least begun, prior to parturition. Administration of the vaccine should be timed ideally such that the host mammal produces a high level (titre) of specific antibodies during colostrum formation. An optimum immunisation schedule in the cow will include giving at least one parenteral administration prior to parturition, preferably about 2-3 weeks in advance.

A useful manner of administering the vaccine to the host animal is by feeding the host animal on a diet containing the vaccine and periodically boosting the immune response by supplementary parenteral administration.

The bacterial strains used in preparing the vaccine of the invention can conveniently and economically be selected from the many strains that have been implicated in causing actual instances of gastroenteric disease. Many samples of such strains are held by hospitals, research institutions and public health laboratories throughout the world, and bona fide workers in this field can have access to such samples readily. Hence there is no difficulty whatsoever in obtaining appropriate bacterial strains from which to prepare the vaccine. However, the invention is not necessarily limited to the use of such naturally-occurring disease-causing organisms, and the current advances in bacterial fermentation and genetic manipulation have made it possible for "synthetic" micro-organisms to be prepared possessing the essential criteria needed for the invention. This would be particularly easy as far as the plasmid-born pili expression criteria are concerned. Nevertheless, in terms of vaccine efficacy, it is still preferable to use naturally-occurring bacterial strains possessing the required criteria, because by so doing the vaccine is likely to induce the host to generate antibodies having specificities to other characteristics of the bacteria that are also related to their disease-causing properties, especially enterotoxins. Such additional characteristics might be lacking in "synthetic" organisms.

It is therefore a preferred feature of the invention that at least one, and more preferably more than one, of the bacterial strains used to prepare the vaccine are naturally-occurring strains that have been implicated in causing gastro-enteric disease in humans.

A preferred embodiment of the invention is an injectable or oral vaccine comprising, in a pharmaceutically acceptable carrier or diluent, antigens of at least one strain of Type I pili-expressing *E. coli* of the serogroups 018 and/or 0125.

Preferably, the vaccine also includes antigens of at least one bacterial strain from one (more preferably both) of the following groups:
(a) CFA I pili-expressing *E. coli* of the serogroups 025 and/or 078;
(b) CFA II pili-expressing *E. coli* of the serogroups 06 and/or 08.

A particularly preferred embodiment of the invention is an injectable or oral vaccine comprising, in a pharmaceutically acceptable carrier or diluent, antigens of an 018 *E. coli* expressing Type I pili, an 078 *E. coli* expressing CFA I pili and an 06 *E. coli* expressing CFA II pili.

Preferably, the vaccine includes antigens of an 0149 *E. coli* expressing K88 adhesion factor. An additional benefit to be obtained from including such antigens is that 0149 *E. coli* are generally observed to be strong producers of both LT and ST toxins, and hence such a vaccine should lead to antibodies that are particularly effective against toxin-producing bacterial strains.

It is also preferable that the vaccine should include antigens of a human gut adherent 0159 *E. coli* or another *E. coli* serotype expressing an antigenically-identical pili type. This serogroup exhibits a mode of gut adhesion that cannot be antigenically associated with any of the above pilus types, although such surface features are evident on the bacterium. This previously unidentified pilus type is also apparently plasmid-mediated and hence probably transmissable. The particular strain of 0159 *E. coli* with which we have worked was obtained from the Central Public Health Laboratory, London, and is described by McConnell, M.M. et al. in *J. Bacteriol*, 1979, Vol. 139, pages 346-355. According to McConnell, the strain was isolated in Canada and reference is made to Gurwith M. J. et al. in *Arch. Intern. Med.*, 1977, Vol. 137, pages 1461-1464. It is identified by the Central Public Health Laboratory designation E2985/76. This particular strain has been deposited by McConnell in the National Collection of Type Cultures (NCTC), Central Public Health Laboratory, 175 Colindale Avenue, London NW9 5HT, UK. The NCTC deposition number for this strain is 11602.

Any mammal is a potential host animal for the purposes of the invention, but it is most preferable that members of the Bovidae, especially cows, and to a lesser extent other domesticated animals whose milk is conventionally used as human food, such as goats, should be employed.

The immune milk from the host mammal can be fed directly to a human infant or adult in order that the recipient can benefit from the immunoglobulins therein. The milk can be in its natural state, or can be processed prior to consumption provided that such processing does not destroy the essential functionality of the immunoglobulins. Controlled pasteurisation and concentration (evaporation) are examples of conventional milk processing techniques that can be used. The milk can be whole milk, skimmed milk, or whey. If serum from the host mammal is recovered as the source of the immunoglobulins, the immune serum can also be fed directly to a human infant or adult. The immune milk or immune serum can be fed in admixture with other materials, and especially with other food ingredients, if desired. Indeed, subject to the proviso that the essential functionality of the immunoglobulins be maintained, the immune milk or immune serum can be incorporated in any human foodstuff in which milk is traditionally an ingredient.

In general, however, it is envisaged that the immunoglobulins will be recovered in concentrated form from the immune milk or immune serum, and that such recovered immunoglobulins will then be used to provide passive immunity. A variety of techniques are now available in the art, by means of which recovery of the immunoglobulins can be effected. One such technique is to separate an immunoglobulin-rich concentrate from the bulk of the milk components, and an example of such a procedure is described in UK patent specification No. 1 573 995. An alternative technique is to separate immunoglobulins from milk or serum by means of chromatographic techniques. Chromatography can provide immunoglobulin-rich fractions in which the immunoglobulins are present in relatively pure (or sometimes completely pure) form. Affinity chromatography in which the immunoglobulins are recovered by being bound to insolubilised antibodies, especially monospecific antibodies (e.g. so-called "monoclonal" antibodies) is preferred. Such a procedure is described in European patent application No. 0059598. After recovery, the immunoglobulin material should be carefully stored prior to use, to preserve its essential functionality. Freeze-drying is an example of a useful technique for rendering the recovered immunoglobulin material storage-stable.

The recovered immunoglobulins can be incorporated in a human foodstuff. Potentially, any foodstuff that does not require subsequent processing (e.g. cooking) which would denature the functional immunoglobulins, can be used as a carrier. A particular embodiment of the invention is an artificial "milk" product, especially such a product intended for consumption by human infants. In general such products are marketed in the form of dry powders and require reconstitution with water to yield a milk-like liquid ready for consumption. Apart from the incorporation of the immunoglobulin material, the composition of the foodstuff need not differ in any way from conventional compositions. By way of example only, such compositions can be based on milk solids, e.g. skimmed milk powder and/or whey powder, together with non-milk materials, or can be formulation entirely from non-milk materials. An example of the latter type of formulation is set out in Example 7. The quantity of functional immunoglobulin material incorporated in the food product is not critical, as long as sufficient is provided in the digestive tract to cause a protective benefit. The minimum effective content in the food product will depend on the functionality of the immunoglobulin material and the quantity of the foodstuff that is likely to be consumed. The minimum effective content can readily be ascertained by one skilled in the art. As the immunoglobulin material itself is proteinaceous and entirely harmless to the human consuming it, there is no upper limit on the inclusion level in the foodstuff, other than the constraints imposed by economics.

As an alternative to artificial milk products, the immunoglobulins can, for example, be incorporated in powdered beverage bases such as soft drink products. Such products will be reconstituble with water to provide, for example, fruit-flavoured beverages. Typical formulations will be based on flavourings such as orange or lemon, plus maltodextrins and sugars.

The immunoglobulins can also be used to provide passive immunity against "traveller's diarrhoea" illnesses acquired whilst visiting foreign countries, for example. Indeed, in this context an immunoglobulin-containing product of the invention can provide a valuable therapeutic benefit in mitigating the effects of any such infection. It is envisaged that an oral product containing the immunoglobulins, for example in the form of pills or capsules, if ingested according to a prescribed schedule, will maintain a protective level of immunoglobulins in the digestive tract of the traveller. Any conventional medicinal encapsulation method can be used, e.g. sugar pills or gelatin capsules.

The bacterial antigen vaccine of the invention can also be used to promote active immunity in the human by being administered directly, so stimulating the natural immune system of the human recipient. In this context, the vaccine can have several modes of application, depending on its precise purpose. For example, as a measure against endemic or epidemic gastro-enteric diseases, the vaccine can be generally administered orally and/or parenterally to adults and infants. If used as a safeguard against gastro-enteric diseases encountered by an individual when travelling to an unusual location, the vaccine can be administered as a single or multiple injection and/or oral inoculation suitably timed prior to the journey. If used as a means of reducing the incidence of neonatal infection in human infants, the vaccine can be administered to the expectant mother on one or more occasions suitably timed during pregnancy so that at birth the mother is producing enhanced amounts of antibodies and hence the colostrum will contain unusually high levels of antibody. In this last embodiment of the invention, the unborn child will also be receiving enhanced antibody levels because in the human the antibodies are transmitted to the foetus via the placenta.

The following procedures can be used to identify strains of enteropathogenic bacteria appropriate for use as the basis of a vaccine in accordance with the invention. These are given by way of example only, as the skilled reader will recognise that such procedures can be modified readily in detail to suit individual laboratory practice and the availability of equipment and other facilities.

Expression of pili

In the first instance the presence or absence of pili on any given strain of bacteria can be determined by examining specimens of the bacteria by means of an electron microscope. At a magnification of about 20,000× any pili expressed by a bacterium will be clearly visible and will give the bacterium a characteristically "spiny" or "hairy" appearance. In contrast, at such magnification a smooth exterior on the bacterium will be indicative that the specimen is not expressing any pili.

Having established that pili are present, it is necessary to determine whether any of the required types is being expressed.

Various crude methods for differentiating between known pili types, such as mannose sensitivity tests and other erythrocyte agglutination procedures, are described in the literature, but for the present purposes we do not consider such procedures to be sufficiently accurate. The natural occurrence, for example, of bacterial strains possessing previously unidentified adhesins introduces ambiguity into such procedures. Instead, we recommend the positive identification of pili types by means of antisera.

Indeed, most workers will prefer to develop antisera to pili types in order that the identification of subsequent strains can be performed more readily. Suitable antisera can be easily prepared once definitive samples of the pili types have been obtained. The following Example illustrates the basic procedures entailed.

EXAMPLE 1

Purified pili were prepared as follows from known pili-bearing strains of *E. coli* that had been obtained from external reference collections or other reputable sources.

The bacteria were grown in roux flasks for 48 hours at 37° C. on CFA agar. CFA agar consists of 1% casamino acids (Difco), 0.15% yeast extract (Difco), 0.005% magnesium sulphate and 0.0005% manganese chloride plus 2% agar at pH 7.4. This medium is described in Evans et al. (*Infection and Immunology*, 1977, Vol 23 p 330). The bacteria were harvested and washed in sterile phosphate buffered saline (PBS). Pili were heat-stripped from the bacteria at 60° C. for 45 minutes in the case of CFA I, CFA II, K88 pili and pili expressed by 0159 *E. coli* strain E2985/76 referred to earlier. In the case of Type I pili the bacterial suspension was additionally disrupted for 1 minute using a homogeniser. The whole bacteria and cell debris were centrifuged at 1000× g, leaving pili in the supernatant liquor. The supernatant liquor was adjusted to pH 4.5 by the addition of acetic acid and left for several days at 4° C. to precipitate the pili. The resultant precipitates were recovered by centrifugation at 35,000×g and resuspended in PBS. Electron microscopic examination revealed the presence of large numbers of pili.

Antisera were prepared in rabbits against the purified samples of pili. Taking the CFA I pili as an example, a total of 2 mg of purified pili were injected subcutaneously in multiple sites in each rabbit using Freund's complete adjuvant. After 4 weeks a boosting injection of 1 mg of pili, again in multiple sites in each rabbit using Freund's incomplete adjuvant, was made. Bleeding was performed after a further two weeks. Absorption to yield monospecific anti-pili sera was carried out using roux flask cultures of non-piliated variants of the three bacterial strains from which the original purified pili samples had been obtained. In this procedure equal volumes of centrifuged, washed bacteria and the sera obtained from the rabbits were incubated together for 15 minutes at ambient temperature and then spun to collect the supernatant.

The resulting mono-specific anti-pili can be used to identify the pili types on further bacterial strains by means of standard bacterial slide agglutination tests.

Enterotoxin production

The identification of strains of enteropathogenic bacteria that produce an abundance of toxins can be effected by obtaining a cell-free preparation of enterotoxins from the bacteria under test and then examining for toxin activity using the suckling mouse assay and the Chinese hamster ovary cell assay.

(a) Preparation of enterotoxins

ST toxins are usually obtained from culture supernatants and LT toxins from culture supernatants or whole cell lysates. There are also published procedures available for the purification of LT and ST toxins, but for the determination of the enterotoxicity of *E. coli* strains by the suckling mouse and the Chinese hamster ovary cell assays separation and purification of the enterotoxins is unnecessary and, as the following example shows, 18-hour culture supernatants of strains grown in media such as Brain Heart Infusion (Oxoid CM225) or synyeast can be used for both tests.

EXAMPLE 2

Synyeast is a semi-synthetic medium comprising 20 g casamino acids, 6.0 g yeast extract, 2.5 g sodium chloride, 8.71 g dipotassium hydrogen phosphate, (0.05 M), and 1.0 ml of trace salts solution dissolved in almost a liter of distilled water, adjusted to a pH of 8.5 with 0.1 N sodium hydroxide and brought to a final volume of 1 liter. The trace salts mixture consists of 5.0% magnesium sulphate, 0.5% manganese chloride, and 0.5% ferric chloride dissolved in 0.001 N sulphuric acid.

Appropriate volumes of the media were dispensed into Erlenmeyer flasks and sterilised at 121° C. for 15 minutes. The flasks were inoculated with starter broth cultures and the bacteria grown aerobically at 37° C. in a shaking water bath for 18 hours. The cultures were then centrifuged to remove the bacteria, and the supernatants containing the enterotoxins poured off and sterilised by millipore filtration.

(b) Heat-stable (ST) toxins

The production of ST toxins by a strain of bacteria can be identified by the following procedure. This technique is based on that of Dean et al. (*J. Infect. Dis.*, 1972, Vol 125 p 407).

EXAMPLE 3

3-day old mice were separated from their mothers shortly before use and divided randomly into groups of 4. The infant mice were injected with 0.1 ml of test material through the body wall directly into the milk filled stomach. Any necessary dilutions of the samples to be tested were done using PBS. One drop of 1% pontamine blue made up in PBS was added to each 0.6 ml of the inoculum and results from mice with no dye in the intestinal tract at autopsy were discarded. After injection the mice were kept for 4 hours and then killed with chloroform. The abdomen of each mouse was opened, the intestines were examined for distention and then removed. The intestines of the 4 mice in each group were weighed together and the ratio of total gut weight to total remaining body weight calculated. A ratio of greater than 0.09 was considered positive, less than 0.07 negative and between 0.07 and 0.09 questionably positive.

(c) Heat-labile (LT) toxins

The production of LT toxins can be determined by the following procedure. This is an adaptation of the procedure described by Guerrant et al. (*Infection and Immunology*, 1977, Vol 10 p 320) which in turn was based on the observation by Hsie et al. (*Proc. Nat. Acad. Sci. USA*, 1971, Vol 68 p 358) that the Chinese hamster ovary clonal cell line CHO-K1 responds with distinct morphological and biochemical changes after treatment with cyclic adenosine monophosphate (AMP).

EXAMPLE 4

Stock cultures of CHO-K1 were grown in Ham's F12 medium supplemented with 10% foetal calf serum and 1% glutamine in an atmosphere of 5% carbon dioxide in air at 37° C. The cell line was passaged by trypsinization with 10% (v/v) trypsin solution in Earles Balanced Salt Solution (BSS) for 15 minutes at 37° C. after washing the monolayer with Earles BSS without calcium and magnesium. The trypsinized cells were resuspended in growth medium. CHO-K1 cells, Ham's F12 medium and Earles BSS are obtainable from Flow Laboratories. For assay, cell suspensions containing approximately 1,000 cells per 0.02 ml in F12 medium plus 1% foetal calf serum were added to each well of a 96-well micro culture plate. Enterotoxin solution (10 micro liters per well) was added immediately after plating. The plates were incubated for 20 hours in an atmosphere of 5% carbon dioxide in air at 37° C. and then fixed with methanol for 2 minutes and stained with Giemsa diluted 1:1 with distilled water. The action of LT enterotoxin induces over 40% of the cells to transform from an epithelial-like cell to a fibroblast-like cell, and hence by counting the number of cells elongated an estimate can be made of the toxins produced by the strain.

Vaccine production

The following example illustrates the production of a vaccine for use in accordance with the invention.

EXAMPLE 5

A considerable number of strains of *E. coli* implicated in causing gastro-enteric diseases were obtained from numerous sources. Such strains can be readily obtained by bona fide workers in this field from hospitals, public health laboratories and academic institutions. The various strains were subjected to the test procedures already described to determine whether they expressed particular pili types and were good toxin producers. The following strains were selected as the basis for a vaccine.

TABLE 1

| E. coli Serogroup | Adhesion | Enterotoxin |
|---|---|---|
| 018 | Expresses Type I pili | −ve |
| 078 | Expresses CFA I pili | +ve(ST + LT) |
| 06 | Expresses CFA II pili | +ve(ST + LT) |
| 0149 | Expresses K88 pili | +ve(ST + LT) |
| 0159 | Expresses human gut adhesive pili antigenically | +ve(ST + LT) |

TABLE 1-continued

| E. coli Serogroup | Adhesion | Enterotoxin |
|---|---|---|
| distinct from the above types. | | |

All 5 strains were cultured on a standard broth and then subjected to a heat strip at 60° C. for 45 minutes to release pili and other useful antigenic factors and hence to maximise response to the vaccine when administered. The vaccine was preserved by the addition of 0.5% formalin.

The vaccine was administered continuously to pregnant cows as part of their diet for a period of six weeks immediately prior to the expected calving date. The oral daily dose was 50 gms of a premix spread onto a standard feed concentrate. The premix comprised by weight:

57% wheat flour (9% moisture)
47% cheese whey powder
4% citric acid
2% centrifuged bacterial slurry containing 20 HI units of each strain per gm of premix.

During the same period each cow was injected intramuscularly in the hip region on three occasions (6 weeks, 4 weeks and 2 weeks prior to parturition) with an injectable vaccine containing a total of 200 Haemagglutination Inhibition units of bacterial matter.

The antibody titre of the milk from each cow over the first four days of lactation was assayed and a clear O-antigen response to each strain injected was observed, indicating that the specificity of the natural antibodies in the bovine milk had been altered by the vaccine. The results are given in Table 2 below:

TABLE 2

| Antibody titres engengered in the early milk of a cow immunized multiparenterally | | | | | |
|---|---|---|---|---|---|
| E.coli serotype | 06 | 018 | 078 | 0149 | 0159 |
| Vaccinate titre | 1000 | 256 | 512 | 4000 | 64 |
| Control titre | 8 | 4 | 16 | 4 | 4 |

The immune milk was also demonstrated to be bacteriostatic, and to inhibit bacterial adhesion in vitro.

EXAMPLE 6

An antibody-rich concentrate was prepared as follows:

Immune bovine milk obtained as in Example 5 was adjusted to pH 3.5 by the addition of hydrochloric acid in order to precipitate casein. Following centrifugation, the resulting supernatant liquor was adjusted to neutral pH by the addition of sodium hydroxide, and an immunoglobulin fraction precipitated by the addition of 40% aqueous ammonium sulphate. The precipitate was centrifuged, resuspended in PBS, subjected to exhaustive dialysis to remove ammonium sulphate, and freeze dried.

EXAMPLE 7

An edible product capable of imparting passive immunity against human enteropathogens was prepared as follows:

An antibody concentrate obtained as in Example 6 was added to a commercially-available powdered milk substitute for human infants having the following composition:

| Ingredient | Parts by weight |
| --- | --- |
| Corn syrup solids | 26 |
| Sucrose | 26 |
| Soy protein isolate | 17.5 |
| Corn oil | 13.9 |
| Coconut oil | 13.9 |
| Calcium phosphate tribasic | 1.5 |
| Potassium citrate | 0.7 |
| Potassium chloride | 0.6 |
| Magnesium chloride | 0.3 |
| Ascorbic acid | 0.1 |
| Trace elements, vitamins, etc. | 0.1 |

The antibody concentrate was included in the formulation at a level sufficient to impart to the milk substitute (when reconstituted with water to a drinkable form) and O-antigen titre of 1 in 256 serotype.

EXAMPLE 8

Evaluation of the therapeutic effect of passively administered bovine antibody in the mouse infection model As many human pathogenic *E. coli* will colonise and proliferate in the mouse intestine, it is possible to use the mouse as a protection model for the human infant. The 018 serogroup *E. coli* adhere very strongly to mouse enterocytes, so these were chosen for study, as there seemed to be little chance that they would clear spontaneously. Infections were established in the mice, and bovine serum antibodies were then administered in an attempt to clear this. The antibodies were administered orally as neat serum.

Materials and Methods

Bovine antisera

The calf was used to raise hyperimmune serum separately to each of the *E. coli* strains selected in Example 5. Calves of approximately 8 weeks of age were given 6 intramuscular injections of 0.1 ml of killed bacteria (dose=approximately 200 HIU), one injection being given weekly for 6 weeks. Blood was collected 2 weeks later by jugular venupuncture. Sera were separated and stored at $-20°$ C.

Mice

6–8 weeks old germ-free Balb-C mice were used throughout.

Procedure

Groups of mice were each orally inoculated with 0.1 ml of a $10^8$/ml overnight nutrient broth culture of individual strains, and kept in a monocontaminated state in sealed cages for 10 days, to allow the bacteria to become established in the intestine.

Faecal samples were taken and viable counts made during this time to verify the monocontaminated state. The mice were kept in sealed cages until day 7, when samples were taken and the cages left unsealed. Antibody treatment began on day 8.

Control Group - the mice were given no bovine antibodies.

Test Group - each mouse was given 0.1 ml of bovine anti-serum three times a day.

Further faecal samples were taken and viable counts made to monitor the progress of the infection.

Dose rates

The bovine anti-serum had haemagglutination titres of 1000 HIU. The group of mice receiving three 0.1 ml oral doses daily were thus each ingesting 300 HIU/day.

Results

It can be seen from Table 3 that the group of mice being dosed three times daily with bovine anti-sera, cleared of infection within 5 days in each case. The control group maintained a high level of infection throughout the experiment.

TABLE 3

| Days after infection | Days after commencement of dosing | Group | 018 Count |
| --- | --- | --- | --- |
| 10 | 2 | Control | $9.0 \times 10^7$ |
|  |  | Test | $1.5 \times 10^8$ |
| 12 | 4 | Control | $6.0 \times 10^6$ |
|  |  | Test | $3.0 \times 10^3$ |
| 15 | 7 | Control | $1.5 \times 10^6$ |
|  |  | Test | 0 |

Bovine anti-sera had been shown to block adhesion to mouse enterocytes in vitro, and it seems probable that this is an important factor in clearing the infection. Adult mice are not sensitive to the two toxins ST and LT, so any anti-toxic activity the sera may have is irrelevant in the mouse infection model. The sera had been shown to have anti-O and anti-pilus activity (by haemagglutination assay and slide agglutination tests respectively); as the anti-sera were raised against a slurry of whole bacteria it would seem likely that there are also antibodies to various other bacterial components. The clearing phenomenon was probably caused by a combination of these effects.

EXAMPLE 9

Evaluation of the therapeutic effect of passively administered bovine antibody in the pig infection model One of the human pathogenic serogroups of *E. coli*, 0149, is also pathogenic in pigs. This serogroup is one of those included in the vaccine of Example 5, and the pig provides a useful animal model in which to evaluate bovine antibody products raised in response to this vaccine. The following experiment was an attempt to protect neonatal piglets from 0149 infection by oral immunisation with bovine antibodies.

Materials and Methods

Bovine anti-0149 serum

The calf was used to raise hyperimmune serum to 0149. Calves at approximately 8 weeks of age were given 6 intramuscular injections of 0.1 ml of killed bacterial (dose=approximately 200 HIU) one injection weekly for 6 weeks. Blood was collected 2 weeks later by jugular venupuncture. Sera were separated and stored at $-20°$ C.

A haemagglutination assay performed on the serum showed it to have an anti-0149 titre of 1000. One piglet dose consisted of 5 ml of serum, i.e. 5000 H.A. units.

Procedure

Samples of serum and colostrum were taken from a gilt and a haemagglutination assay performed to determine their anti-0149 activity. Both samples had an anti-0149 titre of 16 HIU, and this was deemed to be sufficiently low to allow the piglets to suckle, without raising their serum antibody titre to a level high enough to invalidate the experiment. The piglets were left on the gilt for 6 hours. 8 piglets were selected and marked into two groups of four, one group being a control group, and the other receiving anti-0149 serum. This group was dosed with serum every 2 hours during the suckling period.

All piglets were then removed from the gilt and each was given an oral infecting dose of $10^8$ 0149 E. coli. Serum dosing of one group continued at two hourly intervals for a further two days. The interval between doses was then gradually increased over the following 3 days, after which time it was stopped altogether. Faecal swabs were taken daily, and were plated out onto blood agar. The piglets were weighed daily.

Results

The groups being dosed with bovine anti-0149 serum gained weight from the onset of the experiment, even on the first day after the shock of separation and the change to a new diet. The control group, however, lost weight on day 2, the day after separation, and all were dead on day 3. The swabs showed that all of the dead piglets intestines were colonised by large numbers of 0149, whereas at this time, the group being dosed showed very little 0149 on swabs taken. A post-mortem performed on one of the dead piglets showed the intestines to be swollen and fluid-filled, with some haemorrhaging having occurred; symptoms typical of gastroenteritis.

The group being dosed with antibodies continued to gain weight and had all the appearance of normal healthy piglets. Swabs showed the infection to have cleared altogether 4 days after the infection date. Weighing and swabbing were then discontinued: however, weekly inspection of the pigs showed them to be healthy and progressing well.

TABLE 4

| Piglet weights in kg during 0149 protection experiment | | | | | | | | |
|---|---|---|---|---|---|---|---|---|
| | Dose Group (Piglets A-D) | | | | Control Group (Piglets E-H) | | | |
| Day | A | B | C | D | E | F | G | H |
| 1 | 1.55 | 1.6 | 1.45 | 1.30 | 1.1 | 1.3 | 1.3 | 1.45 |
| 2 | 1.60 | 1.7 | 1.50 | 1.25 | 1.1 | 1.3 | 1.15 | * |
| 3 | 1.65 | 2.15 | 1.75 | 1.35 | 0.9* | 1.1* | 0.95* | |
| 4 | 1.90 | 2.30 | 1.80 | 1.50 | | | | |
| 5 | 2.20 | 2.45 | 2.00 | 1.70 | | | | |

The symbol * denotes a death.

TABLE 5

| Presence of 0149 in faecal swabs | | | | | | | | |
|---|---|---|---|---|---|---|---|---|
| | Dose Group (Piglets A-D) | | | | Control Group (Piglets E-H) | | | |
| Day | A | B | C | D | E | F | G | H |
| 1 | − | − | − | − | − | − | − | − |
| 2 | − | ++ | − | + | + | ++ | ++ | * |
| 3 | − | + | − | + | | | | |
| 4 | + | + | − | − | | | | |
| 5 | − | − | − | − | | | | |

+ = 10-20 0149 colonies
++ = confluent 0149 growth
* = a death
− = no 0149 colonies This experiment demonstrated that bovine antibodies afford protection to the neonatal pig. The serum may have anti-toxic activity; this would explain the survival of the pigs, but not the clearing of the infection. Antiadhesive activity would prevent colonisation of the intestine, as would the ability to agglutinate the bacteria. Previous work had shown that bovine anti-serum raised against 0149 has both anti-K88 and anti-0149 activity (shown by slide agglutination and haemagglutination assay respectively). It had also been shown to block adhesion to pig enterocytes in vitro, and to be bacteriostatic. It has also been shown that oral/parenteral immunisation with antigens from heat-inactivated E. coli can give rise to anti-enterotoxin antibodies. It would seem probable that a combination of all of these factors is responsible for protection of the neonatal pig from infection. In a similar control experiment, piglets which were dosed with non-immune bovine serum rapidly succumbed to infection and died within three days, thus clearly demonstrating that normal bovine serum has no protective action in the piglet.

We claim:

1. A process for the preparation of immunoglobulins useful in providing passive protection against E. coli bacteria implicated in causing gastroenteric disease in humans, in which process a host mammal is immunised with a vaccine comprising antigens of a plurality of strains of E. coli collectively expressing Type I pili, CFA I pili, CFA II pili and K88 pili to induce said host mammal to produce substantial quantities of immunoglobulines specific to said antigens, and said immunoglobulines are recovered.

2. An oral composition for humans, comprising in a pharmaceutically acceptable carrier or diluent, immunoglobulins that have been prepared by a process according to claim 1.

3. Immunoglobulines prepared by a process according to claim 1 and recovered in the form of an immune milk.

4. An oral composition for humans, comprising in a pharmaceutically acceptable carrier or diluent, mammalian immunoglobulins that have been prepared by a process according to claim 1.

5. A synthetic milk product for human infants, incorporating immunoglobulins prepared by a process according to claim 1, in an amount sufficient to impart passive protection against E. coli bacteria implicated in causing gastoenteric disease in human infants.

6. A vaccine for oral and/or parenteral administration comprising, in a pharmaceutically acceptable carrier or diluent, antigens of a plurality of E. coli strains collectively expressing at least one virulence characteristic selected from each of the following groups:
    (a) chromosome-mediated pili;
    (b) CFA I pili and CFA I pili;
    (c) K88 pili.

7. A vaccine for oral and/or parenteral administration comprising, in a pharmaceutically acceptable carrier or diluent, antigens of at least one E. coli strain selected from each of the following groups:
    (a) Type I pili expressing E. coli of the serogroups 018 and 0125,
    (b) CFA I pili expressing E. coli of the serogroups 025 and 078; and
    (c) CFA II pili expressing E. coli of the serogroups 06 and 08.

8. A vaccine according to claim 7, additionally comprising antigens of at least one E. coli strain selected from the group consisting of K88 pili expressing E. coli of the serogroup 0149.

9. A process for the preparation of an oral product for humans, capable of imparting passive protection against E. coli bacteria implicated in causing gastroenteric disease in humans, in which process a milk-producing host mammal selected from the group consisting of the Bovidae is immunised with a vaccine comprising antigens of at least one E. coli strain selected from each of the following groups:
- (a) Type I pili expressing E. coli of the serogroups 018 and 0125,
- (b) CFA I pili expressing E. coli of the serogroups 025 and 078, and
- (c) CFA II pili expressing E. coli of the serogroups 06 and 08, to induce the host mammal to produce substantial quantities of immunoglobulins specific to the antigens, milk from the host mammal is collected, and the immunoglobulins are recovered in functional form from the milk and formulated into an orally ingestible product in an amount sufficient to provide passive protection.

10. A process according to claim 9, wherein the vaccine additionally comprises antigens of at least one E. coli strain selected from the group consisting of K88 pili expressing E. coli of the serogroup 0149.

11. A method of reducing the incidence of the neonatal diarrhoea in human infants, in which method immunoglobulins prepared according to the process as claimed in claim 1, are administered to an infant in an amount sufficient to sustain a protective level of immunoglobulins in the digestive tract.

12. A method for reducing the incidence of neonatal diarrhoea in human infants, in which method an infant is fed a synthetic milk product as claimed in claim 5.

13. A method for preventing or mitigating the effects of gastoenteric disease in humans, in which method a human consumes an oral composition as claimed in claim 4.

* * * * *